(12) United States Patent
Faraj

(10) Patent No.: US 6,329,537 B1
(45) Date of Patent: Dec. 11, 2001

(54) TELLURIUM-CONTAINING MOLECULAR SIEVES

(75) Inventor: Mahmoud K. Faraj, Newtown Square, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 0 days.

(21) Appl. No.: 09/504,955

(22) Filed: Feb. 16, 2000

Related U.S. Application Data

(62) Division of application No. 08/832,017, filed on Apr. 2, 1997, now Pat. No. 6,042,807.

(51) Int. Cl.[7] ...................... C07D 301/12; C07D 301/19
(52) U.S. Cl. ........................................... 549/529; 549/531
(58) Field of Search ..................................... 549/529, 531

(56) References Cited

U.S. PATENT DOCUMENTS

| | | | |
|---|---|---|---|
| 4,053,574 | * | 10/1977 | Cull et al. . |
| 4,410,501 | * | 10/1983 | Taramasso et al. . |
| 4,425,448 | * | 1/1984 | Concannon et al. . |
| 4,558,026 | * | 12/1985 | Brill . |
| 4,642,409 | * | 2/1987 | Sato et al. . |
| 4,666,692 | * | 5/1987 | Taramasso et al. . |
| 4,824,976 | * | 4/1989 | Clerici et al. . |
| 4,833,260 | * | 5/1989 | Neri et al. . |
| 4,891,463 | * | 1/1990 | Chu . |
| 5,453,511 | * | 9/1995 | Saxton . |
| 5,466,835 | * | 11/1995 | Nemeth et al. . |
| 5,780,654 | * | 7/1998 | Nemeth et al. . |
| 5,977,009 | * | 11/1999 | Faraj . |

FOREIGN PATENT DOCUMENTS

| | | | |
|---|---|---|---|
| 4425672-A | * | 1/1996 | (DE) . |
| 226257-A | | 6/1987 | (EP) . |
| 266258-A | * | 6/1987 | (EP) . |
| 266825-A | * | 5/1988 | (EP) . |
| 655278-A | * | 5/1995 | (EP) . |
| 2033358-A | | 5/1980 | (GB) . |
| 58-159430-A | | 9/1983 | (JP) . |
| 04-352771-A | * | 12/1992 | (JP) . |
| 08-269029 | * | 10/1996 | (JP) . |
| WO-9634827-A | * | 11/1996 | (WO) . |

OTHER PUBLICATIONS

Millini et al., "Structural Evidence for Isomorphous Substitution in Microporous Materials and Methods of Characterization. The Case of Titanium–Silicalite," Gazzetta Chimica Italiana, vol. 126, pp. 133–140, 1996.*
Sulikowski, "Isomorphous Replacement in the Zeolitic Frameworks: Recent Advances and Implications," Heterogenous Chemistry Reviews, vol. 3, pp. 203–268, 1996.*
Dann et al., "Synthesis and Structure of Cadmium Chalcogenide Beryllosilicate Sodalites", Inorganic Chemistry, vol. 35, No. 3, pp. 555–558, 1996.*
Lindner et al., "Blue–Green Ultramarine–Type Zeolites with Dimeric Tellurium Colour Centers," Inorganica Chimica Acta, vol. 252, pp. 39–45, 1996.*
Miletich, "The Synthetic Microporous Tellurites $Na_2[Me_2(TeO_3)_3] \cdot 3H_2O$ (Me=Zn, Co): Crystal Structure, De- and Rehydration, and Ion Exchange Properties," Monatshefte fur Chemie, vol. 126, pp. 417–430, 1995.
Tuel, "Synthesis, Characterization, and Catalytic Properties of the new TiZSM–12 Zeolite," Zeolites, vol. 15, pp. 236–242, 1995.
Tuel et al., "A new Template for the Synthesis of Titanium Silicates with the ZSM–48 Structure," Zeolites, vol. 15, pp 164–170, 1995.
Reddy et al., "Synthesis of Titanium Containing Silica ZSM–48 (TS–48) using Hexamethonium Hydroxide as Template," Catalysis Letters, vol. 23, pp. 169–173, 1994.
Sheldon, "Synthetic and Mechanistic Aspects of Metal–Catalysed Epoxidations with Hydroperoxides," Journal of Molecular Catalysis, vol. 7, pp. 107–126, 1980.*

* cited by examiner

Primary Examiner—David R. Sample
(74) Attorney, Agent, or Firm—William C. Long

(57) ABSTRACT

Zeolites containing silicon, titanium and tellurium oxides are prepared by a hydrothermal method which yields materials containing exceptionally high levels of catalytically active Ti species. Following calcination, the molecular sieves are active and selective catalysts for the epoxidation of olefins using hydrogen peroxide or organic hydroperoxide. The zeolites may have framework structures of varying topology, including MFI, MEL, BEA, ZSM-48, MTW or MCM-41.

3 Claims, No Drawings

TELLURIUM-CONTAINING MOLECULAR SIEVES

This is a division of application Ser. No. 08/832,017, filed Apr. 2, 1997 now U.S. Pat. No. 6,042,807.

FIELD OF THE INVENTION

This invention pertains to molecular sieves containing silicon, tellurium, and, optionally, titanium oxides. Such molecular sieves are useful as catalysts, particularly in the liquid phase epoxidation of olefins.

BACKGROUND OF THE INVENTION

Siliceous molecular sieves or zeolites wherein certain of the silicon atoms in the crystalline framework have been replaced by titanium atoms are well-known in the art and have been extensively investigated as active and selective oxidation catalysts. For example, U.S. Pat. No. 4,401,501 describes the synthesis of "TS-1" titanium silicalite having a framework structure isomorphous with ZSM-5 (i.e., an MFI topology). Titanium silicalite catalyzes the epoxidation of olefins with hydrogen peroxide, as described in U.S. Pat. No. 4,833,260. In an effort to modify or improve the properties of such materials, the incorporation of additional metal atoms into titanium-containing zeolites has also been attempted. For instance, EP 226,257 teaches a crystalline material of zeolitic character containing silicon, titanium and aluminum oxides. Similarly, EP 266,258 teaches a zeolite material containing silicon, titanium and iron oxides. Zeolites containing oxides of silicon, titanium and gallium are described in EP 266,825. However, there have apparently been no reports to date of a successful preparation of zeolites containing silicon and tellurium oxides or silicon, titanium and tellurium oxides. The catalytic properties of such materials are unknown.

SUMMARY OF THE INVENTION

This invention provides a molecular sieve comprised of oxides of silicon, tellurium, and, optionally, titanium.

DETAILED DESCRIPTION OF THE INVENTION

The present invention relates to a synthetic material containing silicon oxide, tellurium oxide, and, optionally, titanium oxide having a crystalline, porous, structure of zeolitic character. While, as will be explained later in more detail, the topology of these substances may readily be controlled and varied as desired for different end-uses, this invention includes the synthesis of tellurium-containing molecular sieves characterized by framework structures having MFI, MEL, BEA, ZSM-48, MTW or MCM-41 topologies. An MFI framework structure is most preferred where the molecular sieve is to be used as an epoxidation catalyst for a relatively small olefin such as propylene in combination with hydrogen peroxide as an oxidizing agent. In its calcined and anhydrous state, these zeolite materials correspond to the empirical formula: $SiO_2:aTiO_2:bTeO_2$ wherein "a" is typically from 0 to 0.10 (in one embodiment, from 0.005 to 0.10) and "b" is typically from 0.005 to 0.2. Expressed as a percentage by weight of the calcined and anhydrous material, in preferred embodiments of the invention the Ti content ranges from 0.1 to 4.5% and the Te content ranges from 0.05 to 5%. Generally speaking, the activity of the molecular sieve as an olefin epoxidation catalyst will tend to increase as the titanium content is increased within this range.

Without wishing to be bound by theory, it is believed based on analytical characterization of these novel molecular sieves that tellurium atoms (and, where titanium is present, titanium atoms) are substituted for silicon atoms in the framework of a zeolite type framework. In certain preferred embodiments, the molecular sieves are isomorphous with either MFI (ZSM-5), MEL (ZSM-11), BEA (beta), ZSM-48, MTW (ZSM-12), or MCM-41 aluminosilicate zeolites (i.e., zeolites having aluminum and silicon, but not tellurium, atoms present in their framework lattices).

The novel molecular sieves of the invention may be prepared by a process wherein under hydrothermal conditions a derivative of silicon, a derivative of titanium (if titanium oxide incorporation is desired), a derivative of tellurium, and a nitrogenous organic base are reacted. The $SiO_2/TeO_2$ molar ratio of the reactants is desirably greater than 50 but less than 600. The range of from 80 to 140 is particularly advantageous. The $SiO_2/TiO_2$ molar ratio of the reactants in the embodiment where titanium is present is desirably greater than 5 but less than 450, with the range of from 10 to 40 being especially advantageous. The $H_2O/SiO_2$ molar ratio of the reactants is desirably in the range of from 10 to 100, preferably within the range of 25 to 50. Although an alkali metal or alkaline earth metal compound such as an alkali metal hydroxide may also be present, generally it will be desirable to maintain the $M/SiO_2$ molar ratio (where M is the alkali metal or alkaline earth metal) lower than 0.1, preferably lower than 0.01, or (most preferably) equal to 0. The presence of alkali metal or alkaline earth metal cations can lead to the formation of undesirable Ti or Te phases. Preferably, all of the basic ions (e.g., hydroxide) needed in the reaction mixture are supplied by the nitrogenous organic base. Similarly, although oxides of other substances such as aluminum oxides and the like could be introduced into the molecular sieve, the amounts of such other oxides in preferred embodiments of the invention are kept low relative to the amounts of $TiO_2$ and $TeO_2$ which are present. In preferred embodiments, the molecular sieve is aluminum free or essentially aluminum free (i.e., less than 500 ppm Al). The molecular sieve may, for example, consist essentially of silicon oxides and tellurium oxides or silicon oxides, titanium oxides, and tellurium oxides.

Although the silicon derivative may be any substance capable of functioning as a source of $SiO_2$ in a hydrothermal synthesis, such as, for example, fumed silica, silica gel or silica sol, the silicon derivative preferably is a tetraalkyl orthosilicate such as tetramethyl orthosilicate or tetraethyl orthosilicate. Similarly, while the optional titanium derivative may be any substance capable of functioning as a source of $TiO_2$ in a hydrothermal synthesis, such as, for example, a titanium salt (e.g., titanium halide), in preferred embodiments of the invention the titanium derivative is a tetraalkyltitanate where the alkyl groups are the same or different and are $C_1$–$C_6$ alkyl groups such as methyl, ethyl, n-propyl, n-butyl, sec-butyl, iso-butyl, tert-butyl and the like. Tetra n-butyl orthotitanate is a particularly preferred titanium derivative. Likewise, the tellurium derivative may be any substance capable of functioning as a source of $TeO_2$ in a hydrothermal synthesis. While tellurium salts such as halides and hydroxides could be utilized, it is preferred to use tellurium alkoxides where the alkoxide groups are preferably $C_1$–$C_6$ alkoxide groups such as ethoxide, propoxide and the like. In a particularly preferred embodiment, tellurium ethoxide is utilized. Co-precipitates or co-gels comprised of Si and Ti, Si and Te, Ti and Te, or Si, Ti and Te can also be used as starting materials.

The nitrogenous organic base is preferably an alkyl ammonium hydroxide, preferably a quaternary alkyl ammonium hydroxide. The nitrogenous organic base may alternatively comprise a mixture of an alkyl ammonium halide (e.g., tetrapropyl ammonium bromide) and an organic amine (e.g., triethylamine, ethylene diamine). The NOB/SiO$_2$ molar ratio (where NOB=nitrogenous organic base) of the reactants is desirably maintained in the range of from 0.1 to 1, preferably from 0.2 to 0.5. The morphology of the molecular sieve may be controlled as desired by varying the structure of the nitrogenous organic base employed. Without wishing to be bound by theory, it is believed that the cation portion of the nitrogenous organic base functions as a template or structure directing agent. The size and shape of the cation appears to influence the hydrothermal crystallization process such that the framework of the resulting molecular sieve assumes either an MFI (ZSM-5), MEL (ZSM-11), BEA (beta), MTW (ZSM-12), MCM-41, ZSM-48 or other desired topology. For example, the use of tetrapropyl ammonium hydroxide leads to formation of an MFI framework. Where the cation is tetrabutyl ammonium or dialkyl 3,5-dimethyl piperidinium (see WO 96/34827), an MEL structure is produced. To obtain a BEA framework structure, 4,4-trimethylene bis (N-benzyl N-methyl piperidenium) dihydroxide (see U.S. Pat. No. 5,453,511) may be employed. If a tellurium-containing molecular sieve having a ZSM-48 topology is sought, the nitrogenous organic base may comprise trimethylpropylammonium cation or hexamethonium cation. Where the tellurium-containing molecular sieve has an MCM-41 framework structure, an ammonium cation containing a relatively long chain (e.g., C$_{10}$–C$_{18}$) hydrocarbon chain such as cetyltrimethylammonium may be utilized. A tellurium-containing molecular sieve having an MTW framework structure can be prepared using hexamethylene bis (diethyl methylammonium) cation.

The above-described reactants are combined with each other, either sequentially or simultaneously, and the resulting mixture (which may be in the form of a gel) heated in the presence of water at a temperature of from 100° C. to 200° C., preferably from 140° C. to 185° C., at a basic pH (e.g., within the range of 8 to 14) for a time period effective to cause crystals of the desired as-synthesized molecular sieve to form (generally from 1 hour to 10 days, with hydrothermal reaction times of from 6 hours to 3 days typically being preferred). The crystals may be allowed to nucleate spontaneously from the reaction mixture. Alternatively, the reaction mixture may be seeded with crystals of the desired molecular sieve to direct and accelerate the crystallization. The hydrothermal crystallization is usually conducted under pressure and usually in an autoclave so that the reaction mixture is subject to autogenous pressure. The reaction mixture can be stirred or otherwise agitated during crystallization. If so desired, the alcohol(s) derived from the starting reagents may be fully or partially removed by distillation, evaporation or the like prior to hydrothermal treatment. Once crystallization has proceeded to the desired extent, the crystals of as-synthesized molecular sieve may be isolated by any suitable conventional method from the liquid components of the reaction mixture such as filtration, centrifugation, decantation or the like. The as-synthesized molecular sieve will generally contain residual nitrogenous organic base which may be removed by calcination (preferably, in the presence of oxygen) at an elevated temperature (typically, 300° C. to 800° C.) for a period of 0.5 to 24 hours. Calcination also activates the molecular sieve for use as a catalyst.

Prior to calcination, the as-synthesized molecular sieve may be washed with a suitable solvent such as water or alcohol and then dried at relatively low temperatures (e.g., 90° to 150° C. at atmospheric or subatmospheric pressures).

The above-described synthesis method was unexpectedly found to promote the incorporation of higher levels of titanium into the framework of the molecular sieve than is normally possible using conventional hydrothermal procedures in the absence of a tellurium source. The difficulty of achieving greater than 2.5 mole % framework Ti in a silicalite molecular sieve is well known. See, for example, the discussion in Millini et al., *J. Catalysis* 137, 497–503 (1992) and Millini et al., *Gazzetta Chimica Italiana* 126, 133–140 (1996). We have now discovered that the use of tellurium compounds such as tellurium alkoxides appears to facilitate titanium incorporation. Practice of the hydrothermal method described herein has permitted the preparation of molecular sieves containing, according to elemental analysis, cell expansion studies, and catalytic activity measurements, as much as 4.0 to 4.2 mole % framework titanium. Further optimization of the method should permit even higher framework titanium levels to be realized.

The tellurium-containing molecular sieves may be further modified by treatment with a silylating agent or basic substance using any of such methods known in the art to be useful for modification of titanium silicalites, including, for example, the procedures described in U.S. Pat. No. 4,824,976. The tellurium-containing molecular sieves of this invention may be reacted with a compound of general formula X—Si—(—R)$_3$ wherein X is halide,

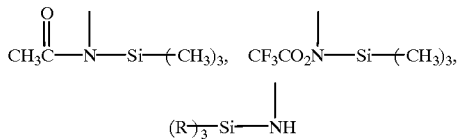

or an imidazolyl group wherein R is an alkyl, aryl or alkyl group. Silylation is preferably performed after caicination.

The tellurium-containing zeolites of this invention have application as molecular sieves for separating compounds based on molecular size or shape and as catalysts in the following reactions: cracking, selectoforming, hydrogenation, dehydrogenation, oligomerization, alkylation, isomerization, dehydration, hydroxylation, and the like. The zeolites containing both titanium and tellurium are particularly useful for catalyzing the same types of oxidation reactions as known titanium zeolites such as TS-1, TS-2, Ti-ZSM-11, Ti beta, and the like. Examples of such reactions include olefin epoxidation, alkane oxidation, phenol hydroxylation, ammoximation of ketones, and the like. As mentioned previously, zeolites may be prepared in accordance with this invention having titanium levels significantly in excess of those readily obtainable by conventional hydrothermal methods. Moreover, the catalytic activity of the zeolite is in most cases directly proportional to the titanium content. This result was surprising, since the relationship between titanium content and activity for the "high titanium" zeolites described in the-prior art becomes increasingly non-linear as the amount of titanium is increased, suggesting that at least some of the additional titanium is being incorporated in a manner not able to function as a catalytic site. The tellurium- and titanium-containing molecular sieves of the present invention, however, may be considered to be more efficient catalysts since substantially all of the titanium present appears to be in active form.

Molecular sieves containing silicon oxides, titanium oxides and tellurium oxides are especially useful catalysts for reacting olefins with an active oxygen oxidizing agent such as hydrogen peroxide or organic hydroperoxide to form epoxides. The amount of catalyst employed to epoxidize an olefin is not critical, but should be sufficient so as to substantially accomplish the desired reaction in a practicably short period of time. The optimum quantity of catalyst will depend upon a number of factors including reaction temperature, olefin reactivity and concentration, oxidizing agent concentration, type and concentration of organic solvent as well as catalyst activity. Typically, however, in a batch type epoxidation, the amount of catalyst will be from 0.001 to 10 grams per mole of olefin. In a fixed bed system, the optimum quantity of catalyst will be influenced by the flow of reactants through the fixed bed (typically, from about 1 to 100 moles per kilogram of catalyst per hour). The concentration of titanium in the total epoxidation reaction mixture will generally be from about 10 to 10,000 ppm.

The catalyst may be utilized in powder, pellet, microspheric, monolithic, extruded, or any other suitable physical form. The use of a binder (co-gel) or support in combination with the titanium-containing molecular sieve may be advantageous. Supported or bound catalyst may be prepared by the methods known in the art to be effective for zeolite catalysts in general.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups. The use of light (low-boiling) $C_2$ to $C_{10}$ mono-olefins such as ethylene, propylene, 1-butene, 2-butene, 1-pentene, cyclohexene, and the like is especially preferred.

The oxidizing agent employed in the process of this invention may be hydrogen peroxide ($H_2O_2$) including compounds which under the epoxidation reaction conditions are capable of generating or liberating hydrogen peroxide. Hydrogen peroxide obtained by operation of any known process may be utilized, including air oxidation of anthraquinone, methyl benzyl alcohol, isopropyl alcohol, and the like. Alternatively, the hydrogen peroxide may be formed in situ, if so desired. For example, the tellurium-containing molecular sieve could be further modified by incorporation of a Group VIII transition metal such as Pd or Pt. Oxygen and hydrogen are then fed to the epoxidation reactor containing the transition metal-modified catalyst. The Group VIII transition metal(s) may be incorporated into the molecular sieve using any suitable method such as, for example, impregnation (preferred), precipitation, blending, or the like. A solution of a Group VIII transition metal in a suitable solvent may be combined with the molecular sieve using an incipient wetness technique, for instance, and the resulting metal-impregnated molecular sieve dried and calcined if desired. Full or partial reduction of the transition metal may be performed prior to use of the molecular sieve as an oxidation catalyst. The amount of Group VIII transition metal supported on the molecular sieve is typically 0.01 to 10 percent by weight, preferably 0.05 to 5 percent by weight calculated as metal relative to the total weight of the catalyst. The methods described in Japanese Kokai Nos. 4-352771 and H8-269029 and in DE 4,425,672 for the preparation and use of transition metal-modified titanium zeolites may be readily adapted for use with the tellurium-containing molecular sieves of this invention.

The amount of hydrogen peroxide relative to the amount of olefin is not critical, but most suitably the molar ratio of $H_2O_2$: olefin is from 100:1 to 1:100. When the olefin contains one ethylenically unsaturated group, the olefin substrate to hydrogen peroxide molar ratio is typically in the range of from 1:10 to 10:1. One equivalent of hydrogen peroxide is theoretically required to oxidize one equivalent of a mono-unsaturated olefin substrate, but it may be desirable to employ an excess of one reactant to optimize selectivity to the epoxide.

Where the molecular sieve has relatively large pores, organic hydroperoxides such as ethyl benzene hydroperoxide, t-butyl hydroperoxide and the like may replace hydrogen peroxide as the oxidizing agent. Suitable reaction conditions will generally be similar to those previously described herein where the oxidizing agent is hydrogen peroxide.

If desired, a solvent may additionally be present during the epoxidation process of this invention in order to dissolve the reactants other than the titanium-containing molecular sieve-catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative examples of other suitable solvents include, but are not limited to, ketones, ethers, aliphatic and aromatic hydrocarbons, halogenated hydrocarbons, and alcohols. Water may also be present in the epoxidation reaction mixture without significant adverse effect.

A basic, neutral or acidic salt containing alkali metal, alkaline earth metal or ammonium cations such as ammonium hydroxide, ammonium acetate, sodium chloride, sodium pyrophosphate, ammonium nitrate, sodium sulfate, potassium hydroxide and the like may be present at low concentrations in order to help improve selectivity to the epoxide.

The reaction temperature is not critical, but should be sufficient to accomplish substantial conversion of the olefin to epoxide within a reasonably short period of time. It is generally advantageous to carry out the reaction to achieve as high a conversion of oxidizing agent as possible, preferably at least 50%, more preferably at least 90% most is preferably at least 95%, consistent with reasonable selectivities. The optimum reaction temperature will be influenced by catalyst activity, olefin reactivity, reactant concentration, and type of solvent employed, among of other factors, but typically will be in a range of from about 0° C. to 150° C. (more preferably, from about 25° C. to 120° C.). Reaction or residence times of from about 1 minute to 48 hours (more desirably, from about 10 minutes to 8 hours) will typically be appropriate, depending upon the above-identified variables. Although subatmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently maintain the reaction components as a liquid phase mixture. For example, performing the epoxidation at elevated pressure will increase the solubility of gaseous reactants such as propylene in the solvent and oxidizing agent. The process of this invention may be carried out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using an active oxygen oxidizing agent will generally also be suitable for use in this process. Once the epoxidation has been carried out to the desired degree of conversion, the epoxide product may be separated and recovered from the reaction mixture using any appropriate technique such as fractional distillation. After separating from the epoxidation reaction mixture by any suitable method such as filtration, the recovered catalyst may be economically reused in subsequent epoxidations. Where the catalyst is deployed in the form of a fixed bed, the epoxidation product withdrawn as a stream from the epoxidation zone will be essentially catalyst free with the catalyst being retained within the epoxidation zone. In certain embodiments of the instant process where the epoxide is being produced on a continuous basis, it may be desirable to periodically or constantly regenerate all or a portion of the used titanium-containing molecular sieve catalyst in order to maintain optimum activity and selectivity. Suitable regeneration techniques include, for example, treating the catalyst with solvent or calcining the catalyst.

EXAMPLES

Example 1

A molecular sieve containing Si, Ti and Te oxides and an MFI framework structure in accordance with the present invention is prepared as follows.

A solution of 22.50 g tetraethylorthosilicate, 2.1 g tetra n-butylorthotitanate, and 0.30 g tellurium ethoxide (85 wt. % in ethanol) is mixed for 30 minutes at room temperature. The solution is then added dropwise to 50 g tetrapropyl ammonium hydroxide (1 M or 20% in water). The resulting mixture is stirred at room temperature for 18 hours, then transferred to a Teflon-lined autoclave. The autoclave is sealed and subjected to hydrothermal treatment in a 175° C. oven for 24 hours. The resulting crystalline as-synthesized molecular sieve is isolated by centrifugation, washed three times with distilled water, dried under vacuum at 120° C. for two hours, and then calcined in air at 510° C. for 6 hours. The calcined molecular sieve contained 41 wt. % Si, 2 wt. % Ti, and 0.2 wt. % Te by elemental analysis. The Si/Ti ratio was 35. No anatase or tellurium oxide phase was detected by x-ray diffraction. The XRD pattern was similar to that of TS-1 titanium silicalite.

Examples 2–7

These examples demonstrate that the molecular sieves of this invention containing titanium are useful epoxidation catalysts. Samples of materials prepared in accordance with the procedure of Example 1, but with varying amounts of titanium and tellurium, were used to catalyze the reaction of propylene with hydrogen peroxide under the following conditions: 0.20 g catalyst, 40 g of a hydrogen peroxide solution containing 3 wt. % $H_2O_2$, 10 wt. % water, 86.5 wt. % isopropanol, 0.1 wt. % formic acid, 0.30 wt. % acetic acid, and 27 ppm diammonium hydrogen phosphate 58° C., one hour. The results shown in Table I were obtained.

Example 8

This example demonstrates the preparation of a molecular sieve in accordance with the present invention containing silicon and tellurium oxides, but not titanium oxide. The procedure of Example 1 is repeated, except that no tetra n-butyl orthotitanate is employed and the quantity of tellurium ethoxide is increased to provide a tellurium content in the final calcined molecular sieve of 7.20 weight % Te.

TABLE I

| Example | Ti, wt % | Te, wt % | $H_2O_2$ Conversion, % | PO Selectivity, % | Acetone Selectivity, % | Propylene Glycol Selectivity, % | PIP Selectivity, % | HHP Selectivity, % | $O_2$ Selectivity, % |
|---|---|---|---|---|---|---|---|---|---|
| 2 | 1.7 | 0.69 | 91.7 | 85.0 | 4.8 | 1.4 | 2.4 | 4.7 | 1.4 |
| 3 | 1.1 | 0.60 | 83.1 | 87.5 | 3.2 | 0.66 | 1.3 | 3.7 | 3.3 |
| 4 | 1.9 | 1.6 | 98.6 | 81.0 | 3.8 | 1.4 | 2.4 | 5.8 | 1.2 |
| 5 | 2 | 4.4 | 97.0 | 82.3 | 3.5 | 1.76 | 3 | 6.8 | 1.8 |
| 6 | 2.7 | 0.17 | 98.4 | 85.7 | 4.9 | 0.8 | 1.5 | 2.85 | 1.7 |
| 7 | 3.8 | 0.30 | 99.5 | 87.5 | 3.8 | 1.1 | 1.95 | 5 | 2.2 |

Examples 9–12

A series of molecular sieves was prepared following the general procedures outlined in Example 1, but varying the proportion of Ti relative to Si in the reaction mixture. In comparative Examples 9–11, the tellurium alkoxide reagent was omitted. The results shown in Table II were obtained.

TABLE II

| Example | Ti, mol % in rxn. mixture | Ti, wt. % in product | Te, wt. % in product | Si/Ti, molar ratio in product |
|---|---|---|---|---|
| 9* | 6.40 | 1.90 | 0 | 36.80 |
| 10* | 8.15 | 1.80 | 0 | 37.70 |
| 11* | 9.80 | 1.80 | 0 | 40.74 |
| 12 | 6.40 | 3.90 | 0.30 | 18.37 |

*comparative (tellurium alkoxide omitted)

In Comparative Example 9, only 1.90 wt. % Ti was incorporated into the final product even though 6.40 mole % Ti was present in the gel formed by combining the tetraalkyl orthosilicate and tetraalkyl orthotitanate. Increasing the mole % Ti in the gel (Comparative Examples 10–11) did not increase the titanium content of the resulting molecular sieve. The use in Example 12 of a tellurium alkoxide in combination with the tetraalkyl orthosilicate and tetraalkyl orthotitanate led to an incorporated titanium content in the product which was approximately twice that of Comparative Example 9, even though the mole % Ti in the gel was not changed. These data confirm that the presence of tellurium alkoxide promotes the incorporation of titanium into the molecular sieve.

I claim:

1. A process for epoxidizing an olefin comprising contacting the olefin with an oxidizing agent selected from the group consisting of hydrogen peroxide and organic hydroperoxides in the presence of a catalytically effective amount of a molecular sieve comprised of Si, Ti and Te oxides.

2. The process of claim 1 wherein the olefin is a $C_2$–$C_{10}$ mono-olefin.

3. The process of claim 1 wherein the molecular sieve is essentially free of Al oxides.

* * * * *